United States Patent [19]

Jarvik

[11] Patent Number: 4,938,766
[45] Date of Patent: Jul. 3, 1990

[54] PROSTHETIC COMPLIANCE DEVICES

[76] Inventor: Robert K. Jarvik, 124 W. 60th St., New York, N.Y. 10023

[21] Appl. No.: 90,995

[22] Filed: Aug. 28, 1987

[51] Int. Cl.$^5$ .............................................. A61F 2/22
[52] U.S. Cl. ...................................................... 623/3
[58] Field of Search ...................... 623/1, 3; 600/16–18

[56] References Cited

U.S. PATENT DOCUMENTS

| | | |
|---|---|---|
| 3,425,064 | 2/1969 | Carnevale et al. . |
| 3,478,695 | 11/1969 | Goranson et al. . |
| 3,491,377 | 1/1970 | Bolie . |
| 3,505,987 | 4/1970 | Heilman . |
| 3,512,183 | 5/1970 | Sharp et al. . |
| 3,513,486 | 5/1970 | DeBennetot et al. . |
| 3,518,702 | 7/1970 | Russa . |
| 3,526,005 | 9/1970 | Bokros et al. . |
| 3,550,162 | 12/1970 | Huffman et al. . |
| 3,553,736 | 1/1971 | Kantrowitz ............................ 623/3 |
| 3,562,352 | 2/1971 | Nyilas . |
| 3,641,591 | 2/1972 | Keiff . |
| 3,656,873 | 4/1972 | Schiff . |
| 3,668,708 | 6/1972 | Tindal . |
| 3,685,059 | 8/1972 | Bokros et al. . |
| 3,733,616 | 5/1973 | Willis, Jr. . |
| 3,911,898 | 10/1975 | Leachman, Jr. . |
| 4,014,318 | 3/1977 | Dockum et al. . |
| 4,015,590 | 4/1977 | Normann . |
| 4,034,742 | 7/1977 | Thoma . |
| 4,041,931 | 8/1977 | Elliott et al. . |
| 4,051,840 | 10/1977 | Kantrowitz et al. . |
| 4,078,267 | 3/1978 | Cieszynski . |
| 4,080,958 | 3/1978 | Bregman et al. . |
| 4,131,604 | 12/1978 | Szycher ................................. 623/3 |
| 4,131,604 | 12/1978 | Szycher . |
| 4,135,494 | 1/1979 | Stoner et al. . |
| 4,143,425 | 3/1979 | Runge . |
| 4,143,661 | 3/1979 | LaForge et al. . |
| 4,152,786 | 5/1979 | Clark et al. . |
| 4,166,466 | 9/1979 | Jarvik . |
| 4,173,689 | 11/1979 | Lyman et al. . |
| 4,173,796 | 11/1979 | Jarvik . |
| 4,187,852 | 2/1980 | Urry et al. . |
| 4,240,409 | 12/1980 | Robinson ............................ 600/16 |
| 4,240,409 | 12/1980 | Robinson et al. . |
| 4,397,049 | 8/1983 | Robinson ............................ 623/3 |
| 4,453,537 | 6/1984 | Spitzer . |
| 4,547,911 | 10/1985 | Strimling ............................ 623/3 |
| 4,573,997 | 3/1986 | Wisman et al. . |
| 4,623,350 | 11/1988 | Lapeyre ............................ 623/3 |
| 4,652,263 | 3/1987 | Herweck et al. . |
| 4,722,350 | 2/1988 | Armeniades ...................... 128/748 |

OTHER PUBLICATIONS

Bregman et al., "Left Ventricular and Unidirectional Intra-aortic Balloon Pumping", The Journal of Thoracic and Cardiovascular Surgery, vol. 68, No. 5, Nov. 1974, pp. 677–686.

Donald et al., "Circulatory Support by a Left Ventricular Balloon Pump", Cardiovascular Surgery 1970, pp. I-96 to I-100.

Ross et al., "The Architecture of the Heart in Systole and Diastole: Technique of Rapid Fixation and Analysis of Left Ventricular Geometry", Circulation Research, vol. XXI, Oct. 1967, pp. 409–421.

Dodge et al., "Usefulness and Limitations of Radiorgraphic Methods for Determining Left Ventricular Volume", The American Journal of Cardiology, vol. 18, Jul. 1966, pp. 10–24.

H. Arvidsson, "Angiocardiographic Determination of Left Ventricular Volume", Acta Radiologica, vol. 56, Nov. 1961, pp. 321–339.

Primary Examiner—Richard J. Apley
Assistant Examiner—James Prizant
Attorney, Agent, or Firm—Edgard H. Haug

[57] ABSTRACT

Implantable prosthetic devices and methods of use for increasing blood flow by increasing arterial compliance and reducing the magnitude of the pressure pulsations in the arterial system, and to increase perfusion of specific organs in order to overcome the deleterious effects of cardiovascular disease, are disclosed.

21 Claims, 8 Drawing Sheets

FIG. 11
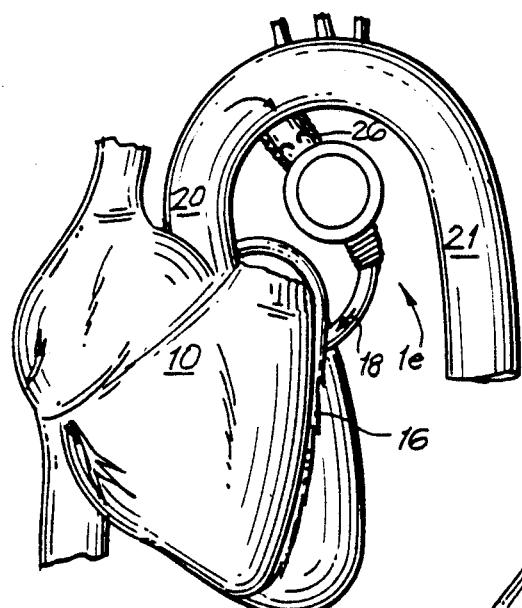
FIG. 12
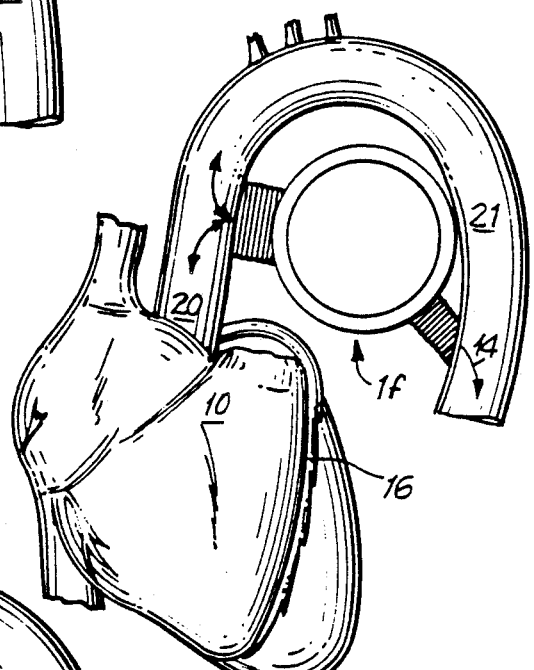
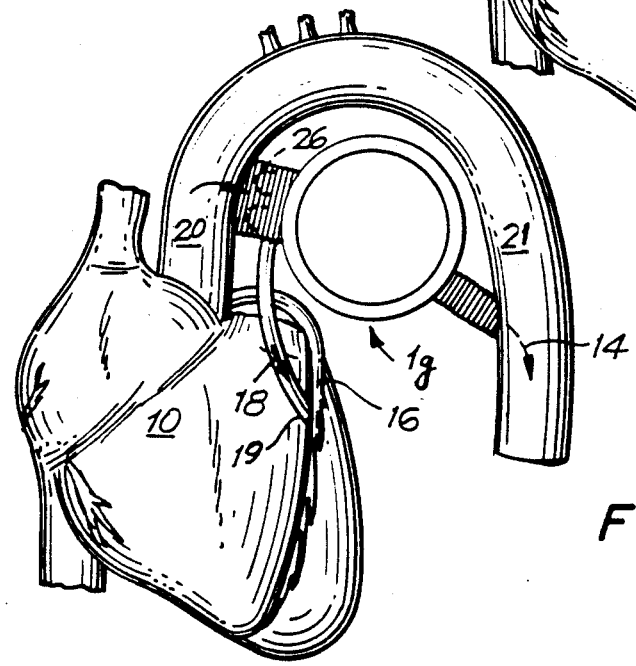
FIG. 13

PROSTHETIC COMPLIANCE DEVICES

FIELD OF THE INVENTION

The present invention relates to implantable prosthetic devices and attendant methods of use to increase blood flow through the arterial system and to reduce the work load on the heart. By this invention a wide spectrum of suitable prosthetic devices including blood vessels, arterial compliance chambers and other means to enhance compliance of the arterial system can be used to assist the cardiac system in combating the devastating effects of arteriosclerosis.

BACKGROUND OF THE INVENTION

Arteriosclerosis is the number one killer in the United States. Close to one million deaths occur annually from heart disease, hypertension and stroke caused by "hardening of the arteries" which inhibits the vital blood supply to the heart muscle, brain, and other tissues. Very often coronary artery disease results from the buildup of ateroscleratic plaques on the inner walls of the arteries which supply blood to the heart muscle. These plaques often contain cholesterol and other materials. They may also become hardened by calcification and become sites for the formation of blood clots which further obstruct blood flow through the arterial system. This debilitating process also occurs in many of the arteries of patients with this disease often resulting in blockage of the carotid arteries to the brain causing strokes.

Arteries attacked by arteriosclerosis are not only narrowed or blocked by the buildup of plaque but also become less elastic as compared to healthy arteries. This condition is frequently described as "hardening of the arteries". Healthy arteries are highly elastic and as the heart pumps blood into the arterial system the arteries expand to receive the increased volume of blood being pumped into them by the heart. As the heart relaxes during diastole (i.e., the filling phase) the normal elasticity of the arteries causes them to contract or decrease in volume thereby forcing blood into and through the capillaries. The natural elasticity of the arteries is known as arterial compliance and provides a blood reservoir for the arterial system into which the heart ejects each stroke volume of blood. By reason of the elastic characteristics of the arterial system, each blood vessel stores energy absorbed during the systolic action of the heart which maintains blood flow between heart beats. When arterial compliance is inhibited or dampened by disease both of these functions (i.e. volume storage and energy storage) are seriously impaired. A condition of decreased arterial compliance requires higher systolic blood pressure to achieve an equivalent blood flow and the effective work load on the heart itself is increased.

Arterial compliance is also extremely important in supplying the proper flow of blood to the heart muscle itself. During systole, blood flow through the coronary arteries is reduced because the myocardium, or heart muscle, is contracting thereby constricting or mechanically "squeezing down" the small arteries and capillaries and limiting the flow of blood through them. During diastole the myocardium relaxes and the small arteries and capillaries located therein open so as to sustain increased blood flow. The compliant aorta and coronary arteries act both as a reservoir for holding the blood which must be pushed through the heart muscle during diastole and, by reason of the energy stored in the walls of these vessels, effectively pump blood through the myocardium during diastole.

With the onset of arteriosclerosis the natural elasticity and compliance characteristics of the arterial system are diminished thereby restricting blood flow and increasing the work load of the heart.

Presently available surgical treatments to overcome this debilitating condition typically involve procedures to either remove the plaque from the inner walls of the vessels or provide blood flow around the plaque through the use of bypass grafts. The first procedure is known as coronary endarterectomy whereby the plaque material which has built up in the larger branches of the coronary arteries is surgically removed. This procedure is time consuming and relatively difficult and does not effectively repair or "clean out" the smaller arteries. Hence, it is infrequently performed and when performed, it is often only with limited success. The second procedure is known as coronary artery bypass grafting which uses vein or artery grafts to supply blood to the coronary artery beyond the site of major obstruction. This procedure is presently used in approximately 250,000 cases per year in the United States alone. Yet another surgical treatment is coronary angioplasty which involves removing or "pushing" the plaque out of the way with a small balloon catheter. Each of these procedures is designed to increase the flow of blood to the heart muscle by eliminating or bypassing obstructions in the coronary arteries.

A need exists for a more efficient and effective method to increase and stabilize blood flow through the arterial system and to decrease the work load on the heart itself without the difficulties and shortcomings attendant to presently known methods of treatment. By the present invention this need has been recognized and satisfied.

SUMMARY OF THE INVENTION

The present invention relates to prosthetic devices and arterial compliance assist devices such as blood vessels with compliant arterial blood reservoir chambers which function to store blood volume and pressure energy resulting from the systolic pressure of the heart, which stored energy can then, in turn, be released to the arterial system during diastole. By these devices peak systolic pressure can effectively be reduced and diastolic pressure and flow increased. Certain preferred embodiments of the invention increase not only mean myocardial blood flow but also decrease myocardial work. As a result, through the use of the present invention the cardiovascular system functions more effectively and the patient's health is substantially improved. In severe cases, the devices of the invention can be used for life saving purposes while in less severe cases the devices can be used to improve the exercise tolerance and overall quality of life of the patient.

The present invention may also be used in conjunction with presently used methods of treatment such as bypass grafts and angioplasty. It should be understood, however, that the present invention is based upon a fundamentally different principle to increase the flow of blood in the arterial system and to the heart muscle. It is further pointed out that the same principle may be used to increase the flow of blood to other organs of the body in patients with extensive arteriosclerosis and also may be used to decrease the work of the heart muscle itself by permitting it to work more efficiently.

OBJECTS OF THE INVENTION

It is an object of the invention to provide implantable prosthetic devices such as arterial blood vessels and chambers which restore or augment the compliance of the natural arterial system to enhance blood flow to vital tissues.

It is another object of the invention to provide prosthetic compliance devices which when surgically implanted in the body will function reliably for a long period of time.

It is a further object of the invention to provide such devices which will function with a minimal incidence of complications including thrombosis and thromboembolism, infection, mechanical failure, calcification, reduction in function due to encapsulation and damage to other adjacent tissues including pressure necrosis or erosion.

It is a still further object of the invention to provide a family of devices adapted to meet varying flow, pressure and anatomic requirements to treat a variety of medical conditions relating to inadequate arterial compliance functions.

Further defining the medical problem addressed as reduced blood flow to a certain organ or tissue due to the effects of arteriosclerosis it is an additional object of the invention to provide prosthetic devices to increase the flow through the diseased blood vessels by increasing diastolic pressure and flow.

A still further object of the invention is to provide devices which store energy during the systolic ejection phase of the heart and, in turn, supply this energy to the blood during the diastolic phase.

Another object of the invention is to provide prosthetic devices which can be easily and inexpensively fabricated using durable blood-compatible materials including but not limited to polymers such as silicones, dacron and polyurethanes and other structural materials including titanium and pyrolitic carbon.

It is a further object of the invention to provide prosthetic compliance devices in which the blood contacting surfaces may be biologic tissues such as living transplanted human blood vessels or preserved animal blood vessels or valves.

It is still a further object of the invention to provide permanently implantable prosthetic devices to enhance the blood flow through diseased arteries which include a pump deriving energy from a source other than the heart such as another muscle within the body or an external power supply.

BRIEF DESCRIPTION OF THE DRAWINGS

Certain preferred embodiments of the invention are disclosed in the following FIGURES:

FIG. 11 is a schematic view of a valved PACC sutured in parallel between the aorta and a coronary artery.

FIG. 12 is a schematic view of a PACC sutured in parallel between the ascending and the descending aorta FIG. 13 is a schematic view of a valved PACC sutured in parallel between the ascending and the descending aorta with a coronary artery bypass graft sutured between the inflow graft of the PACC and a coronary artery.

DETAILED DESCRIPTION OF PREFERRED EMBODIMENTS

Figure 1:
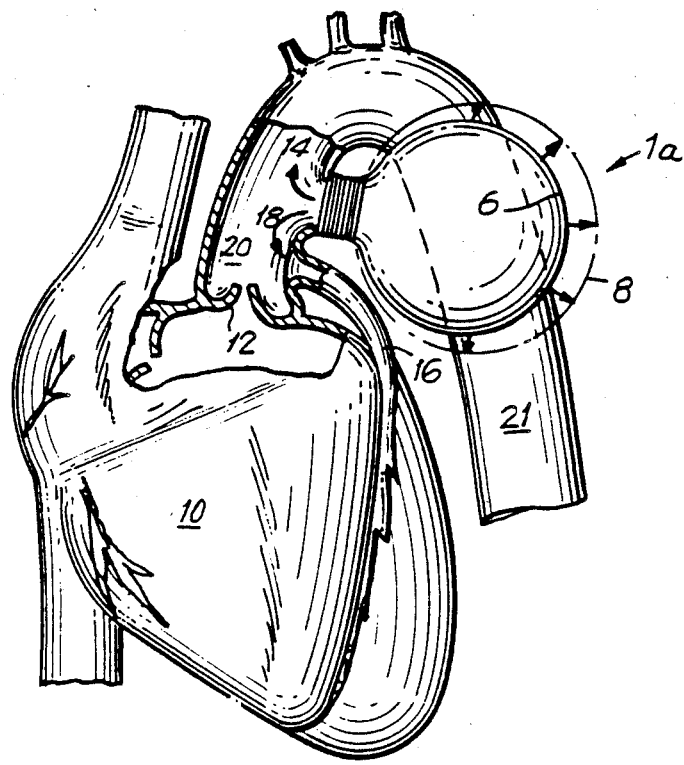
FIG. 1 is a schematic view of a representative prosthetic arterial compliance chamber (PACC) sutured to the ascending aorta.

In principle, a PACC device is a blood containing chamber that changes in volume as a function of the pressure applied. It may be a generally rigid device such as a cylinder with a spring loaded piston, an elastic device such as a stretchable balloon, or a resilient deformable device such as a flattened tube. It must be connected to a blood vessel and accordingly must be designed to avoid blood damage and thrombosis.

It is well known to those skilled in the art that the measurement of blood pressure and the character of blood pulsation in various parts of the vascular system can be utilized as a means of diagnosis of pathological conditions. Techniques for measuring blood pressure and volumetric flow rate at various points in the vascular system are well developed and known to those skilled in the art. For example, blood pressure can be measured by localized catheterization techniques wherein a pressure sensing catheter is inserted into the blood vessel at the point where it is desired to measure the blood pressure. Similarly, the blood volumetric flow rate at a point can be calculated based on measurement of the volume of a section of the blood vessel or organ, such as a chamber of the heart, in the vicinity of the point where the volumetric blood flow rate is to be determined. Well developed techniques for measuring blood vessel and organ size, from which volume can be determined, include various radiographic techniques, such as angiocardiography and ultra-sound.

Based on measurements of the blood pressure and volumetric flow rate at various points throughout the arterial system, the arterial compliance or distensibility of the vessel or organ at the point of measurement can be determined. The parameters are related by the expression:

Compliance=change in volume/change in pressure where the change in volume is the stroke volume or difference in volume between measurements of the systolic volumetric blood flow rate and diastolic volumetric blood flow rate; and the change in pressure is the pulse pressure or difference between the systolic and diastolic blood pressures. The compliance for an individual patient can be assessed and compared to norms determined for healthy individuals. The nature and extent of the pathological condition in the patient being studied can then be diagnosed.

From an assessment of the patient's arterial compliance, a determination of the need for and optimum place of implantation of prosthetic compliance devices according to the present invention can be ascertained. The appropriate volume of the PACC to be implanted at a particular location is determinable from an assessment of the decrease in the patient's compliance compared to normal and the flow requirements to the region involved. The calculated volume for the PACC represents the supplemental blood flow volume provided by the PACC during the interval between systole and diastole to augment the reduced blood flow in the vessel caused by reduced vessel compliance brought on as a result of the pathological condition.

One advantage of the PACC of the present invention is that it can be implanted at essentially any location in the primary arterial system. The only requirement is that the vessel or organ have sufficient diameter at the point of insertion of the PACC to enable the PACC to be safely sutured to the vessel or organ. The implantation of PACC's throughout the arterial system operates as a means for selectively distributing and improving blood flow throughout the arterial system and particularly to increase blood flow to specific target organs whose functions may be impaired by cardiovascular disease.

Hypertension is one symptom of cardiovascular disfunction which can be reduced by appropriate implantation of a PACC. The condition results in part from an increase in the contractions of the smooth muscle within arterial walls. This condition is also caused by disturbances in the hormonal system, by the administration of certain drugs, and as a result of certain psychophysical conditions. Thus, arterial compliance may be functionally reduced in certain hypertensive conditions and the PACC can restore more normal functional compliance.

The PACC can also be used to increase the blood flow to certain target organs whose blood flow is impaired by the existence of a pathological condition. Thus, for example, in advanced stages of diabetes, circulating blood flow to the patient's legs may be become impaired because of increased resistance to blood flow at the capillary level. Implantation of a PACC in the femoral artery can be performed to increase the blood flow to the affected leg.

Similarly, in the case of renal disfunction, a PACC can be implanted from the abdominal aorta to the renal artery in order to provide augmented blood flow to the kidneys.

In certain situations particular embodiments of the PACC, provided with a valve can be utilized to maintain higher blood pressure during diastole than could be maintained without a valve. In valve-equipped PACC's, the valve also serves to prevent backflow, thereby also augmenting flow during diastole.

The PACC can also be used directly as a cardiac assist device. A PACC embodiment utilized for such an application consists of a relatively large compliance volume which is implanted on the aorta close to the heart. In this embodiment, the PACC is fabricated as a single chamber providing the required compliance volume. The device is attached to the blood vessel by means of a single graft which serves for both inflow and outflow. The PACC for this application is not equipped with a valve, since the entire flow is directed in and out of the aorta.

PACC's implanted in major arterial blood vessels to supply increased blood flow to other organs downstream are "in-line" devices which can be either implanted "in series" directly in a section of the blood vessel, or "in parallel" from one blood vessel to another bypassing a section of a blood vessel. Such PACC's therefore, are throughput devices provided with both an inlet and an outlet channel.

With reference to FIG. 1, the prosthetic arterial compliance chamber (PACC) 1a is connected to the ascending aorta 20. The chamber 1 is comprised of a stretchable thin walled polymer balloon which can expand in volume from its smaller or contracted size 6 shown by the solid line to its larger or expanded size 8 shown by the dotted lines, achieved when the left ventricle 10 pumps blood into the aorta during systole. Typically the stroke volume ejected by the left ventricle with one beat may vary between fifty (50) and one (100) hundred cubic centimeters (cc). The stroke volume may be less with heart failure and more in large individuals. For purposes of illustration, a compliance chamber with a maximum change in volume of 35 cc is discussed although larger or smaller devices may be applied to individuals of different sizes or in different anatomic positions for the treatment of different specific disease conditions.

Figure 5:
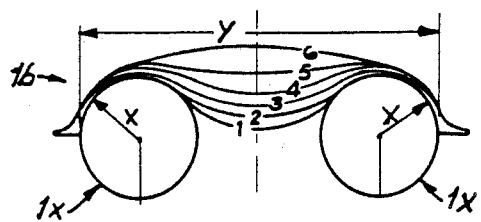
FIG. 5 is a schematic section showing six positions of an arterial compliance chamber wall as shown in FIG. 3 at various pressures and volumes.

When the left ventricle ejects blood into the aorta some of the blood enters the PACC and some blood flows past through the aorta. Depending on the ejection pressure and the time of systole a given volume of blood will be pumped into the PACC. As the volume of blood in the PACC increases pressure energy is stored by the elastic walls of the device. This energy storage may be accomplished in other PACC designs through deformation of spring elements or through magnetic fields In FIG. 5 six positions of a resilient deformable PACC wall are shown which correspond to points on the pressure volume diagram shown in FIG. 6. The device shown in FIG. 5 is generally shaped like a flattened sphere and resembles the biconcave disc geometry of a red blood cell. Typical dimensions are:

toroidal chamber segment 1x has a radius x which is typically 1 cm.;

the diameter y of the toroidal chamber is typically 6 cm.

Figure 6:
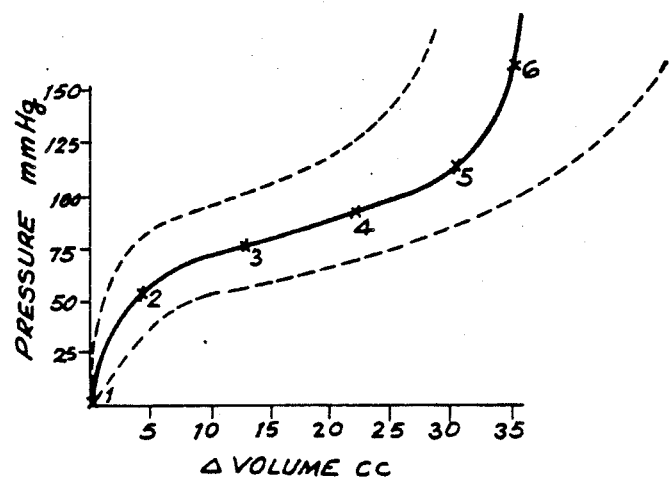
FIG. 6 is a graph showing a typical pressure volume curve of a PACC indicating the pressure and volume relationships at the various wall positions depicted in FIG. 5.

The pressure-volume curve shown in FIG. 6 is also generally representative of the balloon like device shown in FIG. 1. At the end of systole the left ventricle 10 relaxes and the aortic valve 12 closes. The energy stored by the elastic walls of the PACC is then returned to the blood. The PACC then acts as a pump forcing blood into the aorta as illustrated by arrow 14 and also into the coronary artery 16 as indicated by the arrow 18. This increases the pressure in the aorta during diastole, and has the effect of counterpulsation employed with the intraortic balloon pump.

Figures 7, 8:
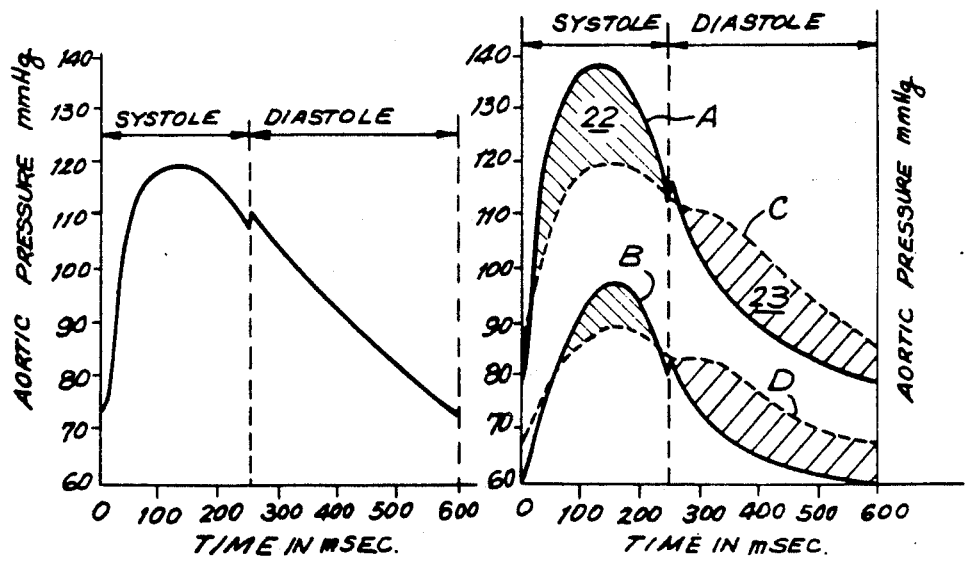
FIG. 7 is a graph of a normal arterial pressure curve in the aorta.
FIG. 8 is a graph showing a series of arterial pressure curves in the aorta, wherein
curve A represents a hypertensive patient with decreased arterial compliance - without a PACC
curve B represents a patient with low blood pressure or in mild heart failure without a PACC
curve C represents the same patient represented in curve A but with a PACC implanted
curve D represents the same patient represented in curve B but with a PACC implanted

FIG. 7 illustrates a typical normal arterial pressure curve. At the heart rate of 100 beats per minute (B.P.M.) the duration of systole is about 250 milliseconds (msec) and the duration of diastole is about 350 msec. During diastole the aortic pressure falls off gradually due to the compliance of the natural aorta and the flow of blood out of the aorta into smaller arteries.

In FIG. 8 curve A represents the aortic pressure of a patient with reduced aortic compliance and mild hypertension. The pressure drops off more rapidly during diastole than it would if the patient's compliance were normal. The function of the PACC is illustrated in FIG. 8C. The peak aortic pressure is lower and the area under the curve 22 represents less work done by the heart (assuming the same stroke, volume in curves A and C). During diastole the PACC pumps blood into the aorta and raises the aortic blood pressure as indicated by area 23 between curve A and C.

In FIG. 8 the effect of a PACC on a patient in mild heart failure is similar to the patient with hypertension, as seen comparing curves 8B and 8C there is a reduction in peak systolic pressure and an increase in diastolic pressure.

Figure 2:
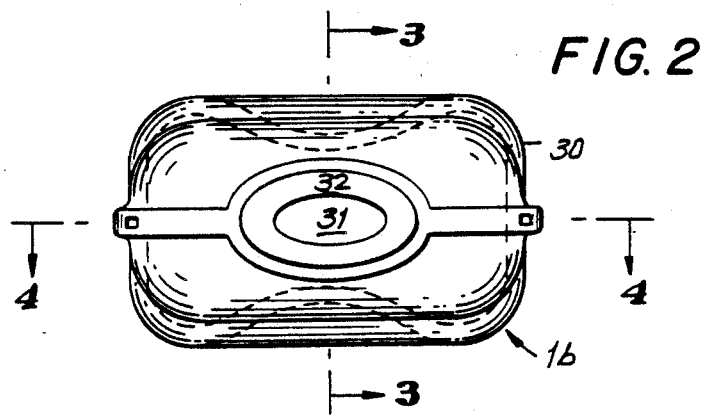
FIG. 2 is an end view of a preferred embodiment of a PACC of the invention having both an inflow and an outflow graft.

FIG. 2 shows an end view of such an "in-line" PACC 1b. The PACC of this embodiment has a generally biconcave shape, analagous in appearance to that of a red blood cell, and has the further feature of inflow and outflow channels along an axis passing transverse to the biconcave sides of the device. The device has dimensions generally represented by FIG. 5.

Figure 3:
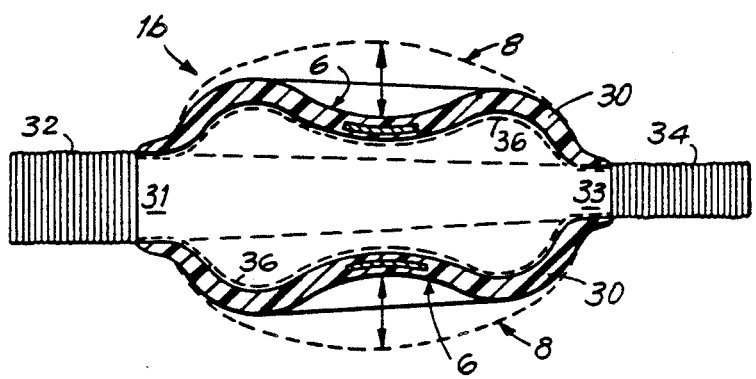
FIG. 3 is a section view of the PACC shown in FIG. 3 taken along the line 3—3.

FIG. 3 is a longitudinal view of the PACC 1b of FIG. 2. The typical length of such a PACC, from end to end, including the inflow channel 31 and outflow channel 33 is 7-9 cm. The inflow and outflow grafts may be short or long depending on the surgical positioning required. The inner wall of the device has a blood surface coating 36. The embodiment shown in FIG. 3, is a PACC in which the inflow channel 31 tapers down to a narrower outflow channel 33 in order for there to be an increased resistance at the outlet. During systole, this reduces flow of blood out of the device while the volume of blood retained within the device is increasing. Such PACC's can also be fabricated with a valve (not shown) at the inlet channel to prevent backflow. The cross-hatched lines show the walls of the PACC in their relaxed position. The dotted lines show the position of the PACC expanded to its full capacity. A PACC of this configuration can be fabricated in larger sizes to provide a total compliance chamber capacity of up to 70 cc or more.

Figure 4:
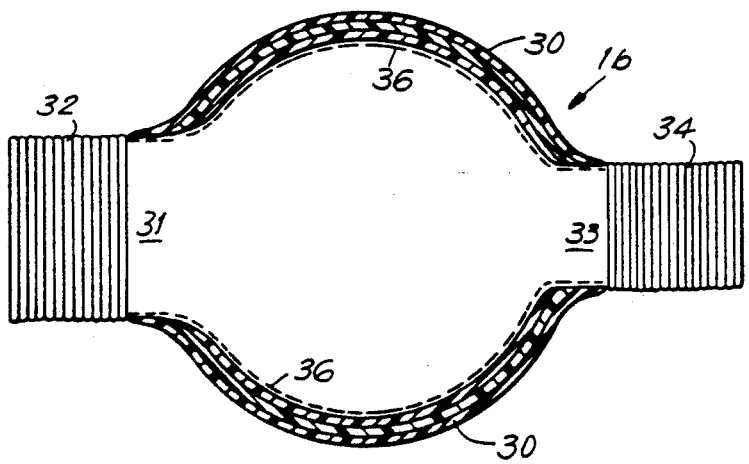
FIG. 4 is a plan view of the PACC shown in FIG. 3 taken along the line 4—4.

FIG. 4 shows a plan view of the PACC 1b of FIGS. 2 and 3.

Figure 9:
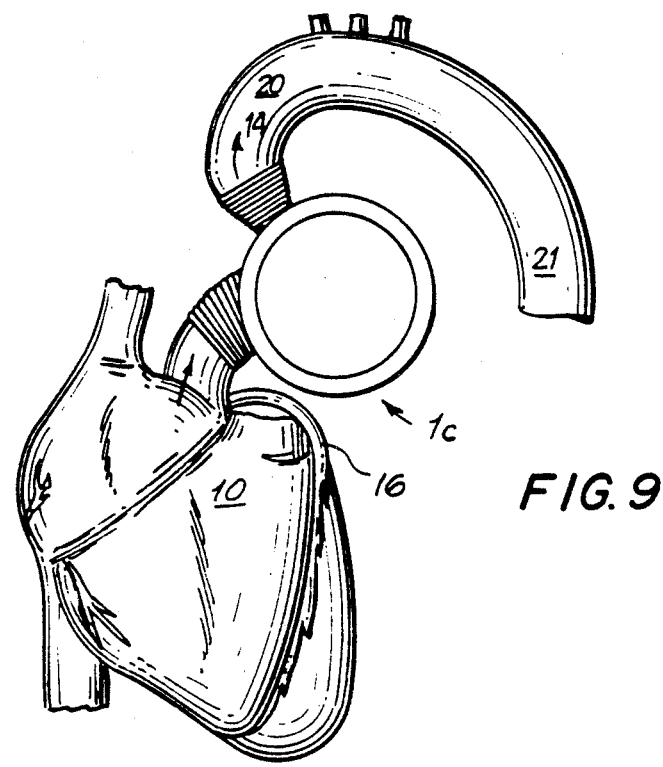
FIG. 9 is a schematic view of a PACC sutured in line with the ascending aorta.

FIG. 9 shows a PACC 1c implanted in series in the ascending aorta. This embodiment directs the compliance chamber capacity to perfuse the ascending aorta 20 and augments the blood flow supplied by the left ventricle 10 to the coronary artery 16.

Figure 10:
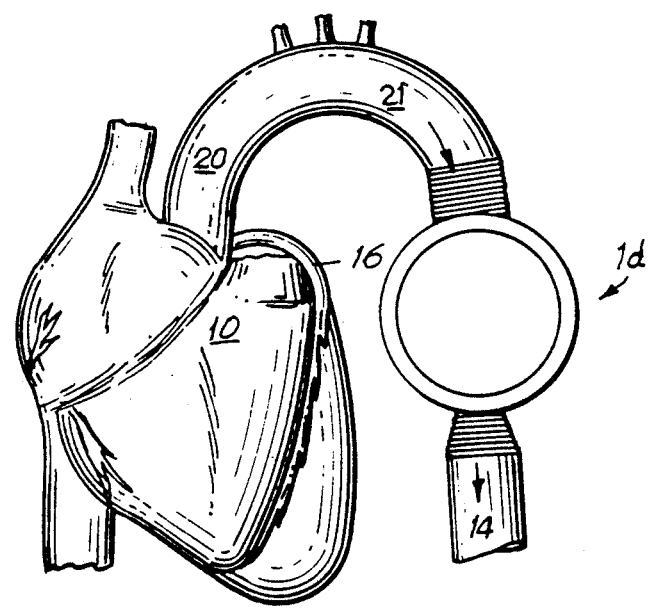
FIG. 10 is a schematic view of a PACC sutured in line with the descending or abdominal aorta.

FIG. 10 shows a PACC 1d alternatively implanted in series in the descending aorta 21. The full compliance chamber volume is similarly directed to perfuse the aorta in this embodiment.

FIG. 11 shows a PACC 1e implanted in parallel between the ascending aorta 20 and coronary artery 16 in order to directly increase blood perfusion to the coronary artery. This embodiment is utilized where compliance of one or more coronary arteries has been reduced by coronary artery disease. This embodiment of the PACC is fabricated with a valve 26 to further increase the diastolic blood pressure to the coronary artery 16, and to prevent backflow of blood.

FIG. 12 shows a PACC 1f implanted in parallel between the ascending aorta 20 and the descending aorta 21. This embodiment permits better washing of the chamber by through flow than other embodiments implanted in the position illustrated in FIG. 1.

FIG. 13 shows a PACC 1g implanted in parallel between the ascending aorta 20 and descending aorta 21, with provision for a take-off 19 from the inflow channel of the PACC to a coronary artery 16. This embodiment is also provided with a valve 26 to increase the blood pressure to the coronary artery and to prevent a backflow of blood. The PACC of this embodiment simultaneously perfuses the descending aorta and a coronary artery with additional blood flow 14, 18, respectively.

PACC's of this invention can, in addition to utilizing the elastic energy of the vessel wall which is imparted from the kinetic energy of the flowing blood during systole and becomes elastic or potential energy held by the expanded vessel wall to be released on diastole, can function utilizing other energy storage sources, such as springs or magnets.

Figure 14:
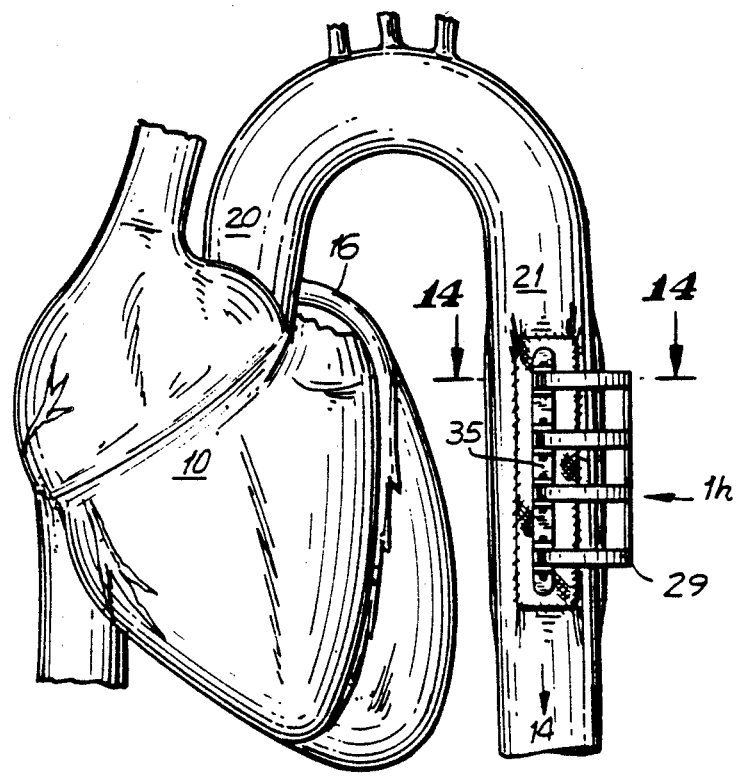
FIG. 14 is a schematic view of a prosthetic device comprising a series of spring clamps surgically attached to the aorta to flatten the vessel and enhance its compliance.

FIG. 14 shows an embodiment of a PACC 1h utilizing spring clamps 29 surgically attached to the aorta to flatten the vessel and enhance its compliance. The size and number of spring clamps utilized in this embodiment is determined as a function of the spring constant. A pusher plate 35 is utilized together with the spring clamps.

Figure 14A:
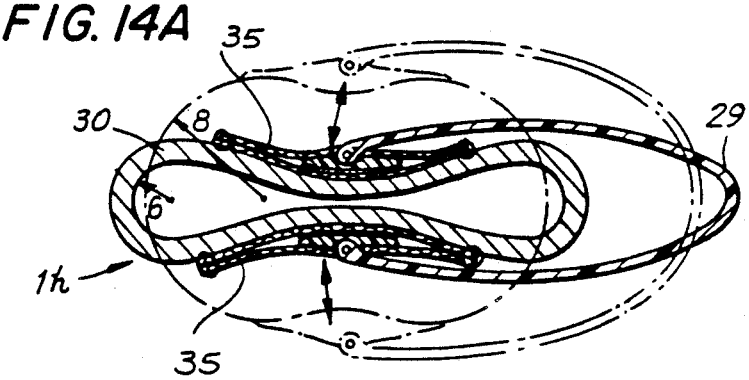
FIG. 14A is a cross-sectional view of the device shown in FIG. 14.

FIG. 14A show a top view of the PACC of FIG. 14 in its end diastolic position 6 in solid lines and in its expanded end systolic position 8 in dashed lines.

Figure 15:
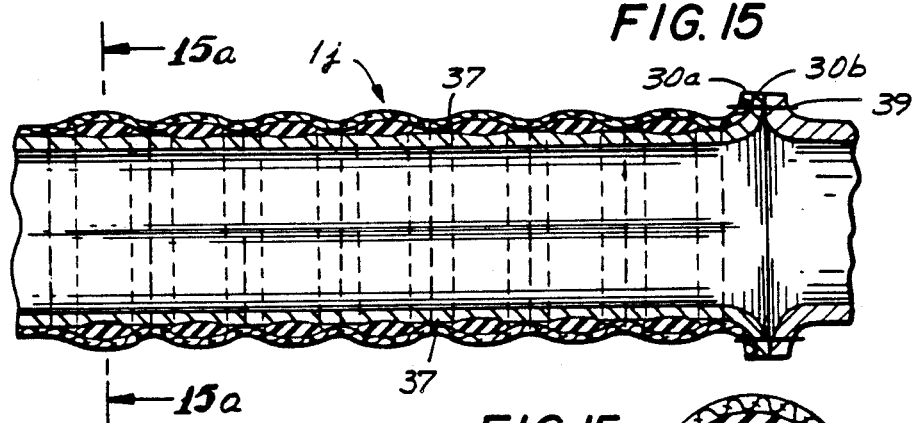
FIG. 15 is a schematic view of a compliant vascular graft with ring-like spring members affixed thereto.
Figure 15A:
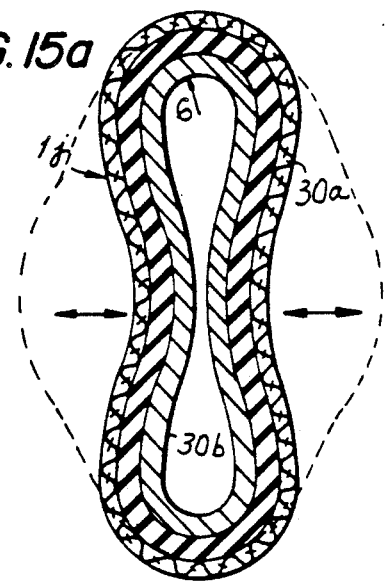
FIG. 15A is a representative polymer ring used as shown in FIG. 15.

FIG. 15 shows a compliant vascular graft wherein ring-like spring clamp members 37 are affixed around a tube-like vascular graft to "flatten" it as shown in FIG. 15A, to provide the required compliance volume. The expanded position is shown by the dotted lines.

The ends of this device consist of double layer fabric grafts 30a, 30b for attachment to the vessel or organ. The device is sutured to the natural artery by means of sutures 39. Each of the individual ring-like spring members 37 consists of an outer polymer-coated ring with a metal spring core.

Figure 16:
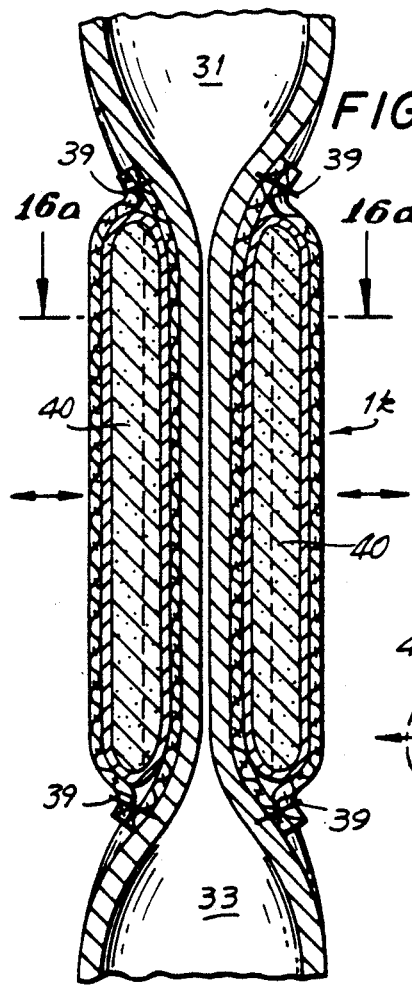
FIG. 16 is a schematic view of a method of increasing compliance of an artery through use of two attracting magnets surgically attached to the aortic wall.

FIG. 16 shows a PACC 1k for increasing arterial compliance through use of two attracting magnets 40 surgically attached to opposite sides of a vessel wall.

Figure 16A:
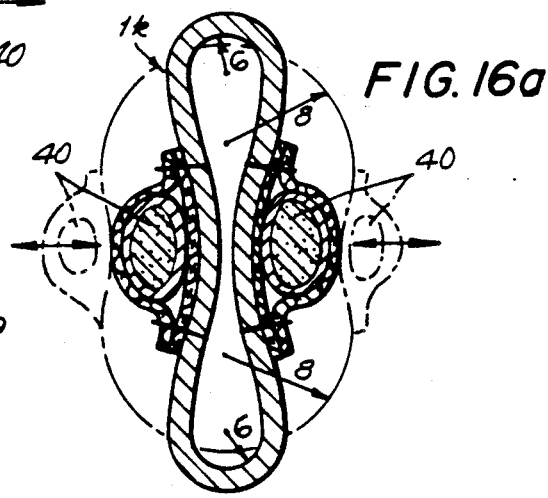

FIG. 16A shows a top view of the PACC of FIG. 16 in its relaxed position in solid lines and in its expanded position in dashed lines.

The magnetically powered PACC of FIGS. 16 and 16A operates by the attractive forces of the two magnets 40 implanted on either side of the device.

During systole as blood enters the PACC the magnets are forced farther apart thus storing energy. During diastole the magnets force the walls of the PACC closer together and pump blood out.

Generally, PACC's of the "in-line" type, having two grafts and two channels can be fabricated in other ways than the toroidal shaped distensible devices 1b–1g of FIGS. 2–13. Alternatively, such "in-line" PACC's can be tubular in design.

Figure 17:
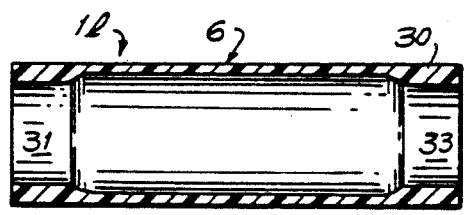
FIGS. 17 and 17A depict a PACC comprised of a distensible elastic tube in its relaxed and expanded state, respectively.

FIG. 17 shows a PACC 1l which is fabricated as a distensible elastic tube. The outer wall 30 is shown in its rest position 6.

Figure 17A:
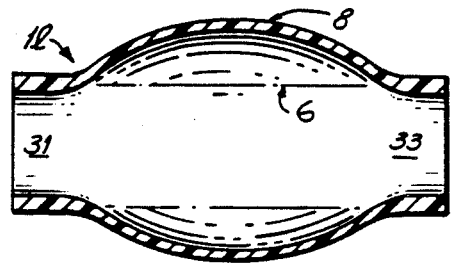

FIG. 17A shows the PACC 1l in its expanded position 8. The device has inflow channel 31 and an outflow channel 33.

Figure 18:
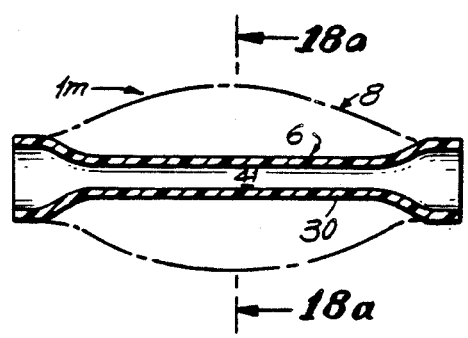
FIGS. 18 and 18A depict a PACC comprised of resilient deformable tube which is generally non-elastic under the pressures it experiences in actual use and a cross-section thereof, respectively.

FIG. 18 show a PACC 1m which is fabricated of a resilient deformable tube shown in its rest position 6 and in its expanded position 8 (dashed lines).

Figure 18A:
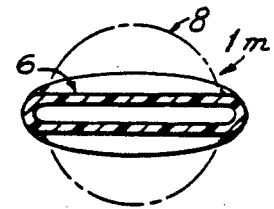

FIG. 18A shows the PACC 1m of FIG. 18 in end view, both in the relaxed state 6 (solid lines) and expanded state 8 (dashed lines).

FIGS. 19, 19A through 22, 22A shown end views of various PACC configurations paired in their relaxed 6 and expanded 8 positions, respectively.

Figure 19:
FIGS. 19, 19A, 20, 20A, 21, 21A, 22 and 22A are various embodiments depicting various shapes and wall thicknesses of PACC's, alternately shown in their relaxed and expanded states.
Figure 19A:
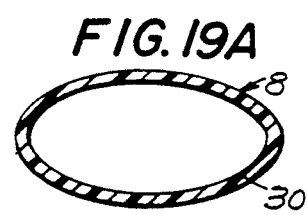

FIGS. 19, 19A show a device having an ellipsoidal cross section.

Figure 20:
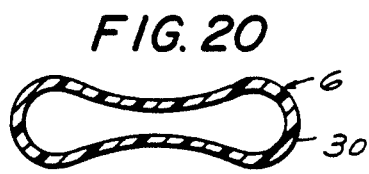
Figure 20A:
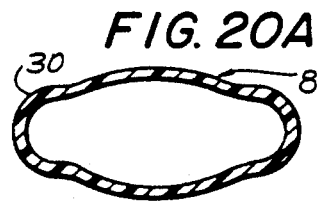

FIGS. 20, 20A show a device having a biconcave shape in cross section.

Figure 21:
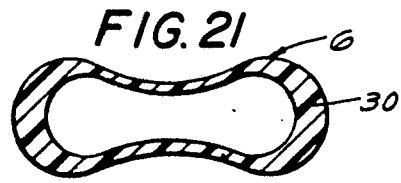
Figure 21A:
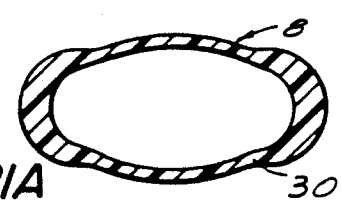

FIGS. 21, 21A shows a device as in FIGS. 20, 20A but having a reinforced wall thickness 30.

Figure 22:
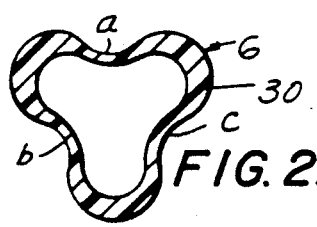
Figure 22A:
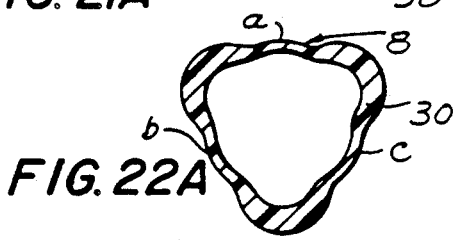

FIGS. 22, 22A show a device having an overall triangular shaped cross section. This device has three wall sections a,b,c which expand to form the compliance volume.

Potential problems that may arise in the use of any implant devices and the means by which such problems are overcome in the use of the PACC's of the present invention are discussed below.

There are four types of problems which may arise in any situation where a prosthetic compliance device is implanted in the arterial system. These potential problem areas include thrombosis; mechanical failure, such as by rupture of the device; loss of compliance due to encapsulation of the device; and calcification.

Thrombosis, or the formation of blood clots, is prevented in the use of the PACC's of the present invention through one or more of a variety of means which include:

by design of the flow geometry of the PACC to eliminate sharp edges and other sites at which blood clots may form and to utilize only smooth geometrical shapes with gradual transitions in the cross sectional area of flow between the inlet and outlet of the device;

by use of a living blood surface on the vessel, aorta, or vein graft;

by assuming high enough flow to prevent stasis;

by utilizing special non-thrombogenic materials of construction for the PACC, such as dacron, silicone, or an elastomeric polyurethane material;

by utilizing a PACC fabricated from animal graft material, such as porcine aorta, by utilizing a PACC which is a transplant of a human aorta;

or by utilizing a PACC of preserved human arterial material such as Aorta, axial or femoral artery.

Harm to the patient due to mechanical failure especially rupture of the PACC itself or of the suture between the vessel or organ and the PACC is prevented in the PACC's of the present invention by means of one or more of the following techniques:

by reducing the stress on any point of the device as well as at the point of juncture to the blood vessel or organ;

by constructing or implanting the device in such a manner so as to cause the forces acting on the device to be bending forces rather than stretching forces;

by fabricating the PACC in such a manner and utilizing such materials that it is of multi-layer construction, made of polyurethane, which is graphite lubricated;

by utilizing radiopaque materials of construction which permit periodic X-ray assessment of continued proper functioning of the device after it has been implanted. If the device is not functioning properly if can be replaced.

Loss of Compliance due to encapsulation of the device by scar tissue is prevented in PACC's of the present invention by one or more of several techniques including:

by implanting the PACC inside the pericardium;

by utilizing fibral coatings on the outside surface of the PACC if it is impermeable;

by utilizing tissue grafts or permeable fabric.

Calcification problems are prevented in PACC's of the present invention by utilizing designs which avoid turbulence and high bending stresses, and by selecting appropriate materials.

The materials of construction of the PACC's of this invention must be such as to be compatible with blood vessels and organs in order to minimize the possibility of rejection and to prevent thrombosis, the formation of blood clots, while maintaining good elasticity and other mechanical properties over the extended period of their implantation. The best materials have been found to be dacron, silicone and elastomeric materials. For embodiments of the PACC's utilizing spring clips, the metallic cores are fabricable from stainless steel. For the embodiments of the PACC's utilizing implanted magnets, the magnets should be rare earth, Co magnets which have a high magnetic flux and the magnets may be hermetically sealed in welded titanium encasements which are not susceptible to corrosion.

The devices of the present invention are utilizable in the treatment and correction of a broad range of conditions. Such applications will be apparent to those skilled in the art from the above disclosure.

I claim:

1. A method for using an arterial compliance assist device having a deformable reservoir for storing blood and absorbing energy during systole and releasing all or a portion of said blood and energy during diastole without utilizing any external energy supply, comprising the steps of:

surgically implanting the arterial compliance assist device in a patient's arterial system;

expanding the arterial compliance assist device during systole to store a quantity of blood pumped by the heart and absorb at least a portion of the energy transferred to the arterial system by the systolic pressure of the heart;

relaxing the arterial compliance assist device during the diastole to release said absorbed energy to assist the flow of blood through the arterial system; and repeating the expanding and relaxing steps.

2. The method as recited in claim 1, wherein the arterial compliance assist device is surgically implanted in the ascending aorta.

3. The method as recited in claim 1, wherein the arterial compliance assist device is surgically implanted in the descending aorta.

4. The method as recited in claim 1, wherein the arterial compliance assist device is surgically implanted in one or more bypass coronary grafts.

5. The method as recited in claim 1, wherein the arterial compliance assist device is surgically implanted in a blood vessel of the arterial system.

6. The method as recited in claim 1, wherein the quantity of blood stored by the arterial compliance assist device is in the range of from 10-40% of the heart stroke volume.

7. The method as recited in claim 1, wherein the quantity of blood stored by the arterial compliance assist device is in the range of 20-50 cc.

8. The method as recited in claim 1, wherein the arterial compliance assist device is constructed of an elastic membrane.

9. The method as recited in claim 1, wherein the arterial compliance assist device is constructed of a durable blood compatible material.

10. The method as recited in claim 1, wherein the arterial compliance assist device is constructed of a polymer such as silicone, dacron or polyurethane.

11. An implantable vascular prosthesis, to improve the effectiveness of perfusion by the cardiovascular system, adapted to store hemodynamic and pressure energy received from arterial blood flow during systole and return said stored energy to the arterial system during diastole, comprising:

a variable volume chamber adapted to receive and discharge blood;

energy storage and actuation means adapted to apply a volume reducing compressive force to the chamber such that as blood is forced to enter the chamber by systolic arterial pressure, kinetic energy is stored as potential energy, and during diastole the stored potential energy actuates means to reduce the volume of the chamber thereby converting said potential energy to kinetic energy and expelling blood from the chamber into the arterial system; and means to anastomose said chamber to the arterial system.

12. The device as recited in claim 11, wherein the deformable chamber is a stretchable elastic membrane.

13. The device as recited in claim 12, wherein the deformable chamber has a continuous, smooth non-circular contour, an intake opening and a corresponding outlet opening, the intake opening being larger than the corresponding outlet opening.

14. The device of claim 11 in which energy is stored through the forced separation of attracting magnetic fields or in which energy is stored through the forced opposition of repelling magnetic fields.

15. The device of claim 11 wherein the deformable chamber comprises one or more spring elements connected to pusher pads affixed to a blood vessel imparting compliance characteristics to said blood vessel.

16. The device of claim 11 wherein said means to anastomose the chamber to the arterial system comprise a single vascular graft through which blood flows both to enter the chamber and to leave the chamber.

17. The device of claim 11 wherein said means to anastomose the chamber to the arterial system comprise two or more vascular grafts.

18. The device of claim 11 wherein a valve is incorporated into the inflow channel to prevent backflow during diastole and one or more outflow vas provided.

19. The device of claim 11 wherein the maximum volume of the device is approximately 20-40% of stroke volume of the left ventricle.

20. The device of claim 11 having a microscopically rough surface to permit tissue ingrowth on either the inside surface, the outside surface, or both.

21. The device of claim 11 wherein natural tissues are utilized to fabricate all or part of the variable volume chamber and the means to anastomose said chamber to the arterial system.

* * * * *